United States Patent [19]

Grosskopf et al.

[11] Patent Number: 4,840,901
[45] Date of Patent: Jun. 20, 1989

[54] RESTRICTION ENDONUCLEASE DRA II

[75] Inventors: Rüdiger Grosskopf, Haar; Christoph Kessler, Munich, both of Fed. Rep. of Germany

[73] Assignee: Boehringer Mannheim GmbH, Mannheim, Fed. Rep. of Germany

[21] Appl. No.: 198,621

[22] Filed: May 20, 1988

Related U.S. Application Data

[63] Continuation of Ser. No. 738,036, May 24, 1985, abandoned.

[30] Foreign Application Priority Data

May 30, 1984 [DE] Fed. Rep. of Germany ....... 3420298

[51] Int. Cl.$^4$ .......................... C12P 19/34; C12N 9/22
[52] U.S. Cl. ......................................... 435/91; 435/199
[58] Field of Search ..................... 435/6, 91, 92, 199, 435/253; 536/27

[56] References Cited

PUBLICATIONS de Wit, C. M., Dekker, B. M. M. and de Waard, A. (1985) FEBS Letters 180(2), 219–223.
Roberts, Richard J. (1984) Nucleic Acids Research 12 (suppl), r 167.
Roberts, Richard J. (1985) Nucleic Acids Research 13 (suppl), r 165.
Grosskopf, R., Wolf, W. and Kessler, C. (1985) Nucleic Acids Research 13(5), 1517–1528.
Purvis, I. J. and Moseley, B. E. B. (1983) Nucleic Acids Research 11(16), 5467–5474.
Maniatis, T., Fritsch, E. F. and Sambrook, J. (1982) Molecular Cloning, a Laboratory Manual, Cold Spring Harbor N.Y., pp. 479–487.
Mise, K. and Nakajima, K. (1985) Gene 36(3), 363–367.

*Primary Examiner*—Thomas G. Wiseman
*Assistant Examiner*—Charles L. Patterson, Jr.
*Attorney, Agent, or Firm*—Felfe & Lynch

[57] ABSTRACT

The present invention teaches a restriction endonuclease which recognizes and cleaves palindromic sequence 5' Pu G G N C C Py 3'

3' Py C C N G G Pu 5' as well as a process for obtaining this endonuclease. One source of the endonuclease is *Deinococcus radiophilus* DSM 20551 (ATCC 27063). The endonuclease is useful in analysis of DNA molecules.

5 Claims, No Drawings

RESTRICTION ENDONUCLEASE DRA II

This application is a continuation of application Ser. No. 738,036 filed May 24, 1985, now abandoned.

The present invention is concerned with a new Type II restriction endonuclease, Dra II, with a process for obtaining it and with the use thereof.

Type II restriction endonucleases are endodesoxyribonucleases which recognise certain DNA sequences and are able to cleave them. Phosphodiester bridges are thereby hydrolysed in the target sequence, namely, one in each polynucleotide strand. Type II restriction endonucleases are, therefore, valuable for the analysis of DNA molecules.

Specific Type II restriction endonucleases are admittedly already known for numerous DNA sequences but there is still a need for the provision of further Type II restriction endonucleases which are specific for DNA sequences which have hitherto not been recognised by any of the known restriction endonucleases.

Therefore, it is an object of the present invention to provide a new restriction endonuclease which is able specifically to recognise and to cleave a sequence which has hitherto not been recognised by any such enzyme.

Thus, according to the present invention, there is provided a restriction endonuclease which is characterised by the palindromic recognition sequence:

```
5' Pu G |G N C  C Py 3'
3' Py C  C N G|G Pu 5'
```

This enzyme preferentially has the point of cleavage defined by the arrow but other points of cleavage are also possible within this sequence.

The new Type II restriction endonuclease according to the present invention, which is hereinafter called Dra II, has a temperature optimum at 37° C. and a pH optimum at 8.2. Further optimum reaction parameters are 25 mM NaCl, 8 to 12 mM $Mg^{2+}$ and 1 mM DTT. The presence of $Mg^{2+}$ is necessary for the activity of the enzyme.

An enzyme which is isoschizomeric to Dra II is now known.

As mentioned above, the enzyme acts upon palindromic structures, thus it recognises a selfcomplementary nucleic acid sequence in which the complementary strand of the double strand has a sequence identical to the one running in the opposite direction.

The recognition sequence can be confirmed by the complete digestion of the DNA's of the plasmid pBR 322, of the virus SV40 and of the phage lambda with Dra II.

Dra II cleaves pBR 322 DNA at positions 524, 1438, 1480 and 4343 within the sequences A G G C C C C, G G G T C C T, A G G A C C C and A G G C C C T. Fragments of the lengths 2863, 915, 543 and 42 base pairs (bp) thereby result.

Dra II cleaves SV40 DNA at positions 523, 2194 and 2753 within the sequences G G G A C C T, G G G C C C T and G G G G C C T. Fragments of the lengths 3033, 1671 and 539 bp thereby result.

Dra II cleaves lambda DNA at positions 2815, 28797 and 48473 within the sequences G G G A C C T, G G G T C C C and G G G T C C T. Fragments of the lengths 22982, 19640, 2815 and 29 bp thereby result.

The fragments specifically obtained by Dra II digestion of the three analysed DNA's and clearly shown in agarose and polyacrylamide gels show that Dra II recognises the cleavage point Pu G G N C C C Py.

The recognition sequence and cleavage point within the recognition sequence of the enzyme can be ascertained as follows: The DNA of the plasmid pBr 322 is linearised with EcoRI by cleavage at position 4361 (statement of position referred to the (+) strand). Both strands of this linearised DNA are marked terminally in two parallel, different reactions. The (−)-strand is phosphorylated on the 5′-end at position 2 with gamma ($^{32}$P)-ATP and T4 polynucleotide kinase. In the second reaction, the complementary (+)-strand is extended by 2 nucleotides at position 4361 with alpha-($^{32}$P)-dATP and Klenow polymerase. In order to achieve a uniform length of the marked (−)-strand, it is further incubated with non-marked dATP and Klenow polymerase. The (+)-strand thus terminates at position 4363. Both differently marked DNA's are subsequently cleaved with Bam HI at position 378.

From the thus resulting 5′- and 3′-terminally marked fragments (3986 (5′)/3988 (3′) and 377 (5′)/379 (3′); length of the marked individual strands) is isolated, respectively, the 3986 (5′) and 3988 (3′) fragment (position 380 up to and including position 2 (5′), position 376 up to and including position 4363 (3′)). The 3′-marked fragment is sequenced. In addition, an aliquot of each of the isolated 3986 (5′) and 3988 (3′) fragments is cleaved with the enzyme Dra II according to the present invention and the length of the 5′- and 3′-marked individual strands determined in the sequence gel by comparison with the 3′-sequence director. On the 5′-terminal marked strand there is thereby given the cleavage position 4348 and on the 3′-terminal marked strand the cleavage position 4344.

The length determination of the 5′-marked (−)-individual strand of the Dra II-Eco RI fragment takes place in the following way:

The (−)-individual strand 5′-marked at position 2 runs identically with the inner and thus 3′-positioned G at position 4345 of the 3′-sequence conductor within the recognition sequence 5′A G G C C C T 3′. Therefore, the 5′-marked individual strand terminates with the nucleotide G of the (−)-strand at position 4348 of the recognition sequence. Thus the cleavage point of Dra II on the 5′-marked (−)-strand is between the nucleotides G at position 4348 and G at position 4347.

The length of the complementary 3′-marked (+)-individual strand of the Dra II Eco RI fragment is determined analogously. The (+)-individual strand 3′-marked at position 4363 runs identically with the outer and thus 5′-positioned G at position 4344 of the 3′-sequence conductor within the recognition sequence 5′A G G C C C T 3′. Thus, the 3′-marked individual strand terminates with the nucleotide G of the (+)-strand at position 4345 of the recognition sequence. The cleavage point of Dra II on the 3′-marked (+)-strand is thus between the nucleotides G at position 4344 and G at position 4345.

According to the present invention, Dra II is obtained by culturing *Deinococcus radiophilus* DSM 20551 and the enzyme recovered from the cells. For obtaining the enzyme, there can be used the conventional biochemical methods of purification, whereby, in the particular fractions obtained, the presence of the enzyme can easily be demonstrated on the basis of the cleavage of its recognition sequence. As substrate there can be used, for example, pBR 322-DNA. The DNA fragments obtained are separated electrophoretically in agarose gels in the buffer systems conventional for fragment separation, in the presence of ethidium bromide.

The micro-organism used for obtaining the enzyme *Deinococcus radiophilus,* DSM 20551 (ATCC 27603), grows aerobically in TGYM medium ATCC 679. The cells occur individually or in pairs, in non-uniform tetrahedra or cubic units in more than one plane. The diameter of the cells is from 1.0 to 2.5 μm. On agar there are formed pink to red, smooth, slightly convex colonies with uniform edges. The organism is gram positive. The cell walls consist of galactose, glucose, mannose, alanine, glutamic acid, lysine, glucosamine and muramic acid. The main component is a peptidoglycan.

Optimal growth conditions are 10° to 30° C., pH 7.0, the doubling time being about 2 hours.

In a preferred embodiment of the process according to the present invention, the cells are digested and the extract is centrifuged for 45 minutes at 13000 r.p.m. For the digestion, there can be used conventional mechanical methods, for example high pressure dispersion or ultrasonics.

The high purification of an ammonium sulphate fraction containing the new enzyme preferably takes place by affinity chromatography, chromatography over anion exchangers and rechromatography on an affinity column. As anion exchangers, there can be used carrier materials based on Sepharose, cellulose or synthetic polymers modified with diethylaminoethyl groups.

For the affinity chromatography, carrier-fixed heparin, for example heparin-sepharose, has proved to be especially useful.

The following Examples are given for the purpose of illustrating the present invention:

EXAMPLE 1

*Deinococcus radiophilus* ATCC 27603 is cultured in TGYM medium at 30° C. for 20 hours and harvested in the late log or stationary phase. TGYM medium has the following composition: 5.0 g. trypton, 1.0 g. glucose, 3.0 g. yeast extract, 0.5 g. D,L-methionine and 1 liter distilled water. The yield is about 150 g. dry mass/100 liters of medium.

24 g. of cell paste are suspended in 60 ml. of digestion buffer (TEMG buffer; 40 mmol/liter tris/HCl (pH 8.0/4° C.); 0.1 mmol/liter EDTA; 7 mmol/liter 2-mercaptoethanol and 10% glycerol). The cells are then digested once by high pressure dispersion in a precooled pressure cell at 1100 bar. The activity is about 100,000 U Dra II. The digestion suspension is subsequently centrifuged for 45 minutes at 13,000 r.p.m. and at 4° C. The precipitate is discarded, the enzyme being present in the supernatant.

EXAMPLE 2

The supernatant obtained according to Example 1 is chromatographed over a heparin sepharose column (2×18 cm.). After washing with 5 volumes of TEMG buffer, the enzyme is eluted with a linear gradient of 0 to 1.0 mol/liter sodium chloride. The enzyme appears in the fractions with 0.1 to 0.3 mol/liter sodium chloride. The fractions are combined and dialysed against TEMG buffer. The dialysate is chromatographed over an anion exchanger column (DEAE-cellulose DE 52 (Whatman); 1×18 cm.) equilibrated with TEMG buffer. After washing with 5 volumes of TEMG buffer, the column is eluted with a linear gradient with 0 to 0.4 mol/liter sodium chloride. The enzyme appears in the fractions with 0.15 to 0.35 mol/liter sodium chloride. The active fractions are combined and dialysed against TEMG buffer. The dialysate is rechromatographed over a heparin-sepharose column (1×10 cm.).

After washing with 5 volumes of TEMG buffer, the enzyme is eluted with a linear gradient with 0 to 0.5 mol/liter sodium chloride. The active fractions are combined and dialysed against 20 mmol/liter tris/HCl buffer (pH 8.0) containing 0.1 mmol/liter EDTA, 10 mmol/liter 2-mercaptoethanol, 100 mmol/liter sodium chloride, 50% glycerol and 0.01% thesit. There are thus obtained about 70,000 U of enzyme.

Activity determination:

Unit definition:

1 U Dra II completely cleaves 1 μg. pBR 322-DNA within 1 hour at 37° C. in 25 μl.

Into a mixture of 12.5 μl. incubation buffer, containing 0.02 mol/liter tris/HCl buffer (pH 8.2/37° C.), 0.02 mol/liter magnesium chloride, 0.05 mol/liter sodium chloride and 0.002 mol/liter dithioerythritol are introduced 6.5 μl. water and 5 μl. pBR 322-DNA (4 OD/ml. extinction (optical density) E=4 at 260 nm and corresponding to a concentration of about c=0.2 mg./ml.), as well as 1 μl. Dra II solution (1 U/μl.). The solution is kept at 37° C. for 1 hour, cooled on ice and mixed with 5 μl. of cold stop solution, containing 7 M urea, 20 wt./vol. % saccharose, 0.06 mol/liter EDTA and 0.01 wt./vol. % bromophenol blue. It is then separated electrophoretically on 1% agarose gel for 3 to 4 hours at 100 V. The bands obtained are identifed in comparison with a DNA length standard.

It will be understood that the specification and examples are illustrative but not limitative of the present invention and that other embodiments within the spirit and scope of the invention will suggest themselves to those skilled in the art.

We claim:

1. Restriction endonuclease which recognizes palindromic sequence

and cleaves said palindromic sequence at a point between the second and third base from the 5' end.

2. Restriction endonuclease according to claim 1, characterised by a temperature optimum at 37° C. and a pH optimum at 8.2.

3. Method for the recognition and cleavage of the DNA sequence 5'-PuGGNCCPy-3' comprising contacting a sample of DNA with a restriction endonuclease which recognizes said sequence and cleaves it at a point between the second and third base from the 5' end under conditions favoring recognition and cleavage of said DNA by said endonuclease and detecting the products of said cleavage.

4. Method of claim 3, wherein said conditions are a temperature of about 37° C. and a pH of about 8.2.

5. Endonuclease of claim 1, wherein said endonuclease is purified from cultured *Deinococcus radiophilus* DSM 20551 (ATCC 27603).

* * * * *